(12) United States Patent
Clark

(10) Patent No.: US 6,369,883 B1
(45) Date of Patent: Apr. 9, 2002

(54) SYSTEM AND METHOD FOR ENHANCED MASS SPLICE MEASUREMENT

(75) Inventor: Brett G. Clark, Whites Creek, TN (US)

(73) Assignee: Amherst Holding Co., Wilmington, DE (US)

( * ) Notice: Subject to any disclaimer, the term of this patent is extended or adjusted under 35 U.S.C. 154(b) by 0 days.

(21) Appl. No.: 09/548,724

(22) Filed: Apr. 13, 2000

(51) Int. Cl.$^7$ .............................................. G01N 21/00
(52) U.S. Cl. ...................... 356/73.1; 356/213; 356/215; 356/236; 250/228; 385/52
(58) Field of Search ................................ 356/73.1, 213, 356/215–216, 226, 229, 234, 236; 250/226, 228; 385/49, 52, 88–90, 14

(56) References Cited

U.S. PATENT DOCUMENTS

| | | | |
|---|---|---|---|
| 4,183,666 A | * 1/1980 | Tahara et al. | ............... 356/73.1 |
| 4,360,268 A | * 11/1982 | Zucker et al. | ............. 356/73.1 |
| 4,391,517 A | * 7/1983 | Zucker et al. | ............. 356/73.1 |
| 4,639,130 A | 1/1987 | Koike et al. | |
| 5,399,877 A | 3/1995 | Carter et al. | |
| 6,181,856 B1 | * 1/2001 | Burn | ............................ 385/52 |

FOREIGN PATENT DOCUMENTS

| | | | |
|---|---|---|---|
| JP | 63-285441 | * | 11/1988 |
| JP | 03-119302 | * | 5/1991 |

OTHER PUBLICATIONS

Tosco, Federico, *Fiber Optic Communications Handbook*, Second Edition, 1990, pp. 739–746.

* cited by examiner

Primary Examiner—Frank G. Font
Assistant Examiner—Sang H. Nguyen
(74) Attorney, Agent, or Firm—Banner & Witcoff, Ltd.

(57) ABSTRACT

The present invention introduces system and method for an enhanced mass splice measurement system for testing a plurality of optical fiber splices and also the reliability of the mass fusion splicer itself. In one embodiment, a first light signal may be transmitted through each of a plurality of optical fibers at one end. At the other end, the plurality of optical fibers may be optically coupled to an integrating sphere using a fiber holder and an adapter. A light meter may be coupled to the integrating sphere for measuring the first light signal received at the integrating sphere. Once the first light signal has been measured, the fiber holder having the ends of the optical fiber may be removed from the integrating sphere and/or adapter and installed in a mass fusion splicer. A second fiber holder having ends of a second fiber cable may be installed in the mass fusion splicer. The mass fusion splicer is used for splicing the plurality of optical fibers of the first cable with the plurality of optical fibers of the second cable. The opposite ends of the second cable may also be coupled a third fiber holder that may be further coupled to the integrating sphere. A second light signal may be transmitted through the plurality of spliced optical fibers and the received second light signal may be measured at the integrating sphere. By taking the difference between the received first light signal and the received second light signal, a true loss at a splice point can be accurately and efficiently determined.

29 Claims, 8 Drawing Sheets

SYSTEM AND METHOD FOR ENHANCED MASS SPLICE MEASUREMENT

FIELD OF INVENTION

The present invention relates to optical fibers and more particularly, the present invention relates to an enhanced mass splice measurement system for testing a plurality of optical fiber splices and also the reliability of the splicer itself.

BACKGROUND OF INVENTION

In present wired telecommunications systems, fiber optic cables have become the standard transmission line through which large quantities of data can be transmitted in the form of infrared light. A standard fiber optic cable is made up of a plurality of individual fibers generally made from multi-component glass, quartz, synthetic resins and/or other material. The individual fibers are generally placed within a plurality of plastic and/or metal tubes. The plurality of plastic or metal tubes may be bundled together and further protected by outer and inner jackets made of metal, plastic, Kevlar, rubber and/or any combination thereof.

Like many other cables, due to manufacturing and/or practical limitations, only limited lengths of fiber optic cable can be placed on a single reel. Accordingly, the fiber optic cable may need to spliced together several times with other fiber optic cables to reach the desired destination. Splicing is accomplished by either fusing or melting two optical fibers together using a fiber optic splicer or, in the alternative, by using a mechanical connection to attach the individual fibers together. Although splicing is preferred, splicing the glass fibers together introduces losses as the light is reflected and/or possibly refracted at the splice points. Accordingly, it is desirable to determine the integrity of the splice and thus, the reliability of the splicer itself (i.e., which optical fiber splicers produce splices with minimum losses at the splice points). Although most modern splicers are able to estimate splice losses, but to accurately determine splicer reliability, actual or true loss is desirable.

FIGS. 1–3 illustrate conventional methods for determining the reliability of fiber optic splicers. FIG. 1 illustrates a conventional method for measuring splice loss and determining splicer reliability utilizing Optical Time Domain Reflectometers (OTDR) 101, 105. As illustrated in FIG. 1, fiber optic cable 102 is spliced with fiber optic cable 104 at splice point 103 using any of the known mass fiber fusion splicers (not shown). In this example, both fiber optic cables are twelve (12) fiber ribbon cables. After the individual fibers are prepared (i.e., outer/inner protective jackets and/or buffer tubes are removed, individual fibers cleaned and cleaved, etc.), pigtails 107, 108 are attached to the ends the individual optical fibers within the cables 102 and 104, respectively. A pigtail can be, for example, a small section of a single optical fiber that includes an optical connector at one end, and can be connected to a single fiber in the cable via a fusion splice or a mechanical connection. After the pigtails 107, 108 are connected to the cables 102, 104, respectively, the connectorized ends of the pigtails 107, 108 are attached one at a time to the OTDR 101. After the first pigtail is connected, the OTDR test on the cables 102, 104 may begin. OTDR 101 launches a plurality of short high-powered light pulse into the optical fibers and receives back scattered and/or reflected light. The received light signal is displayed on an oscilloscope of the OTDR 101 indicating power loss as a function of the length of the fiber optic cable in a graph format. Accordingly, based on the information displayed OTDR's 101 oscilloscope, the distance of the entire fiber optic cable and light losses can be determined. After the test on the first optical fiber has been completed, the connected pigtail must be disconnected and the next pigtail is connected to the OTDR 101 to test the second optical fiber. Accordingly, to measure loss at the splice point 103 for individual fibers, each optical fiber must be attached to the OTDR via its respective pigtail and tested one at a time. Thus, for a twelve (12) fiber ribbon cable, the above described procedure must be performed twelve times causing this procedure to be highly time consuming. Since, OTDR measurements are direction dependent, it is desirable to perform an OTDR test from both ends of the spliced cable and then average the results to determine the reliability of the optical splicer. The above-described conventional method is disadvantageous because connecting each of the plurality pigtails one at a time to the OTDRs 101 and 105 and performing the OTDR test on each individual fiber from both sides is labor intensive and can be time prohibitive. In addition, loss measurements using OTDRs tend to be less accurate for very long fiber runs. Further, OTDRs commonly require minimum fiber lengths of 50 meters or more making small scale testing impractical. As a general rule, OTDRs tend to be less accurate than other systems using power meters and light sources.

FIG. 2 illustrates another conventional method for measuring the splice loss and determining splicer reliability. As illustrated in FIG. 2, OTDR 101 is connected to a 1:12 (i.e., for example, 1 input and 12 outputs) optical switch 201. Using this method, pigtails 107 connected to fiber optical cable 102 are connected to the outputs of the optical switch 201. Pigtails 108 connected to fiber optic cable 104 are connected to the outputs of 1:12 optical switch 202. OTDR 105 is connected to the input side of the optical switch 202. Under this method, once all the pigtail connectors are connected to their respective optical switch 201, 202, the OTDR test may begin. Once all the pigtails 107, 108 are connected to the optical switches 201, 202 respectively, the optical switches 201, 202 are individually operated to complete the OTDR test on each of the optical fibers. In this example, the OTDR test can be performed on the individual fibers without having to manually attach and then remove each pigtail connector to the OTDRs 101 and 105 one at a time. While this method may be more time efficient in determining the losses at splice point 103 than the method as previously described in conjunction with FIG. 1, it suffers from other drawbacks. For example, the method as described with respect to FIG. 2 is disadvantageous in that the introduction of the optical switches 201, 202, at both ends, causes additional reflections to be seen by the OTDR which results in inaccuracies.

FIG. 3 illustrates yet another conventional method for measuring splice losses and splicer reliability. As illustrated in FIG. 3, a laser 301 is connected to the output side of an 1:12 optical switch 302. The pigtails 107 connected to the first ends of fiber optic cable 102 are connected to the output side of optical switch 302. Similarly, pigtails 108 connected to the first ends of fiber optic cable 104 are connected to an input side of a 12:1 (i.e., for example, 12 inputs and 1 output) optical switch 303. The output end of optical switch 303 is connected to a light meter 305.

To determine true loss at splice point 103 and splicer reliability, using the method illustrated in FIG. 3, it is required that reference measurements be taken at splice points 103 for both cables 102 and 104, prior to any splicing. A reference measurement for cable 102 may be taken by coupling a light meter (not shown) to the second ends of cable 102 (i.e., at splice point 103). This method requires connecting or splicing pigtails (not shown) to the second ends of the optic cable 102 and further coupling each of the pigtail connectors to the optical switch. Reference measurements are taken by the light meter (not shown) at splice point 103 by cycling the optical switch to permit the transmission of light generated by laser 301 through each of the optical fibers. The laser 301 transmits light signal at a predetermined power level and the received power level is measured using a light meter. The above process is repeated to obtain a reference measurement for cable 104 at splice point 103. These reference measurement readings respectively represent the loss of the optical switches, pigtail connectors and splices, and the total loss through each of optical fibers. The reference measurement readings indicating the power loss across each of the optical cables and associated hardware (i.e., pigtails, optical switches, etc.) are recorded and used as a reference to determine the true loss of splice point 103 once optical fibers 102 and 104 have been spliced together.

Referring again to FIG. 3, the conventional method for determining the true loss of the fiber optic splices using lasers and light meters will now be described. In this case, after reference measurements are taken as described above, cables 102 and 104 are be spliced together at splice point 103. It is required that the optical switches 302, 303 be configured to permit the light transmitted by laser 301, on the selected fiber at switch 302, to be received by the light meter 305 on the same optical fiber as selected by switch 303. For example, if the optical switch 302 is set to permit the laser 301 to transmit light on the fourth output of the optical switch 302, then the optical switch 303 must be set to receive the light at the light meter 305 on the fourth input. If the two optical switches are not so coordinated, the proper measurement at light meter 305 will not be measured. The light meter 305 receives the transmitted light signal from laser 301, and a user records the power level received at the light meter 305. Accordingly, the total loss through the cables 102, 104, optical switches 302 and 303, pigtails 107 and 108, and splice point 103 along a single fiber may be determined by subtracting the received power level at light meter 305 from the transmitted power level by laser 301. Finally, the loss of the optical splice at splice point 103 can be determined by subtracting the reference measurements from the total loss. Although this may result in more accurate splice measurements and splicer reliability as compared to those of FIGS. 1 and 2, this method is disadvantageous in that substantial effort and time is required to make individual reference measurements as described above. Attaching pigtails to each of the optical fibers at splice point 103, taking measurements, re-cleaning and re-cleaving the fibers for splicing is extremely labor intensive and time consuming. In addition, if the optical switches are not properly coordinated, improper measurements may occur. Furthermore, optical switches float (i.e., the losses introduced by optical switches may vary over time) making it more difficult to accurately determine the reliability of the optical splicer. Although optical switches having more predictable losses are available, such switches tend to be cost prohibitive for many applications.

Thus, what is needed is a time efficient, cost effective and accurate method for measuring splice losses as well as the reliability of the splicer itself. What is also needed is a fiber optic testing method that provides accurate power loss readings and reduces the need for manual calculations.

SUMMARY OF THE INVENTION

In operation, embodiments of the present invention disclose a time, labor and cost efficient system and method for testing the reliability of optical splices. The disclosed embodiments permit rapid and accurate reference measurements for a plurality of optical fibers while minimizing additional equipment and their corresponding losses. Splicing efficiency is also improved since ends of the plurality of optical fibers can be placed in a mass fusion splicer without further cleaving, cleaning or other preparation. Testing efficiency may be further improved by simultaneously transmitting light through more than one optical fiber and mathematically determining the losses on each of the optical fibers. The reliability of the optical splices determined by the disclosed method and system corresponds to the reliability of the optical splicers.

Under embodiments of the present invention, optical fibers are simultaneously connected to the integrating sphere coupled to a light meter. Losses introduced by the additional pigtails and the floating losses of the second optical switch are eliminated. The configuration under the present invention is additionally advantageous since losses can be determined even more efficiently by mathematical calculations and/or coupling the light meter to an intelligent device.

The present invention introduces a system and method for enhanced fiber optic splice measurement and for determining the reliability of fiber optic splicers. In one embodiment, a signal may be transmitted through each of a plurality of optical fibers at one end. At the other end, the plurality of optical fibers may be coupled to an integrating sphere. A light meter may further be coupled to the integrating sphere for measuring the signal quantity received at the integrating sphere. Accordingly, a reference measurement representing the received quantity of signal at the integrating sphere may be determined in an efficient manner without removing and attaching each of the fibers from the light meter. In embodiments of the present invention, the second ends of the plurality of optical fibers may be coupled to a fiber holder. The fiber holder may be coupled to the integrating sphere either directly or via an adapter. In any event, a first reference measurement reading at the integrating sphere may be taken according to embodiments of the present invention.

In alternative embodiments of the present invention, first ends of the plurality of optical fibers may be connected to an optical switch. The optical switch may permit transmission of an optical signal through each of the plurality of optical fibers to the integrating sphere. In embodiments of the present invention, the optical switch may be switched manually or automatically without user intervention. In embodiments of the present invention, the light meter may record the signal level received at the integrating sphere and based on the transmitted signal level, automatically calculate a loss for each of the individual fibers. In embodiments of the present invention, the light signal may be transmitted through more than one optical fiber simultaneously and the reference measurements and/or losses through each may be mathematically calculated or interpolated using known techniques. In yet alternative embodiments of the present invention, the light meter, for example, may automatically indicate whether the calculated loss for the individual fibers is within an acceptable range.

Embodiments of the present invention further introduce an efficient method for measuring signal losses through optical fibers including a splice point and for determining the reliability of a fiber optic splicer. In one example, the fiber holder having a plurality of optical fibers may be removed from the integrating sphere and placed in a mass splice optical fiber splicer. A second holder having first ends of optical fibers from a second cable may further be placed in the mass fiber splicer for splicing with the first cable. Accordingly, the optical fibers in the first fiber holder may be spliced with the optical fibers in the second fiber holder utilizing the mass splicer. In embodiments of the present invention, second ends of the second fiber optic cable may be coupled to a second fiber holder. The second fiber holder may be coupled to the integrating sphere coupled to a light meter for measuring received signal at the integrating sphere. Accordingly, a second reference measurement reading may be taken at the integrating sphere. By taking the difference between the first reference measurement reading and the second reference measurement reading, a true loss at the splice point as well as the reliability of the fiber optic splicer may be determined.

Although the invention has been defined using the appended claims, these claims are exemplary and limiting to the extent that the invention is meant to include one or more elements from the system and methods described herein. Accordingly, there are any number of alternative combinations for defining the invention, which incorporate one or more elements from the specification (including the drawings, and claims) in any combinations or subcombinations.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

Illustrative systems and methods for testing and splicing optical fibers will be described according to the present invention. Embodiments of the present invention as described herein illustrate a simplified and efficient system for determining the reliability of optical splices prepared using an optical splicer. The reliability of the splices utilizing the systems and methods of the present invention correspond to a simplified and efficient system for determining the reliability of optical splicer itself.

Figure 1:
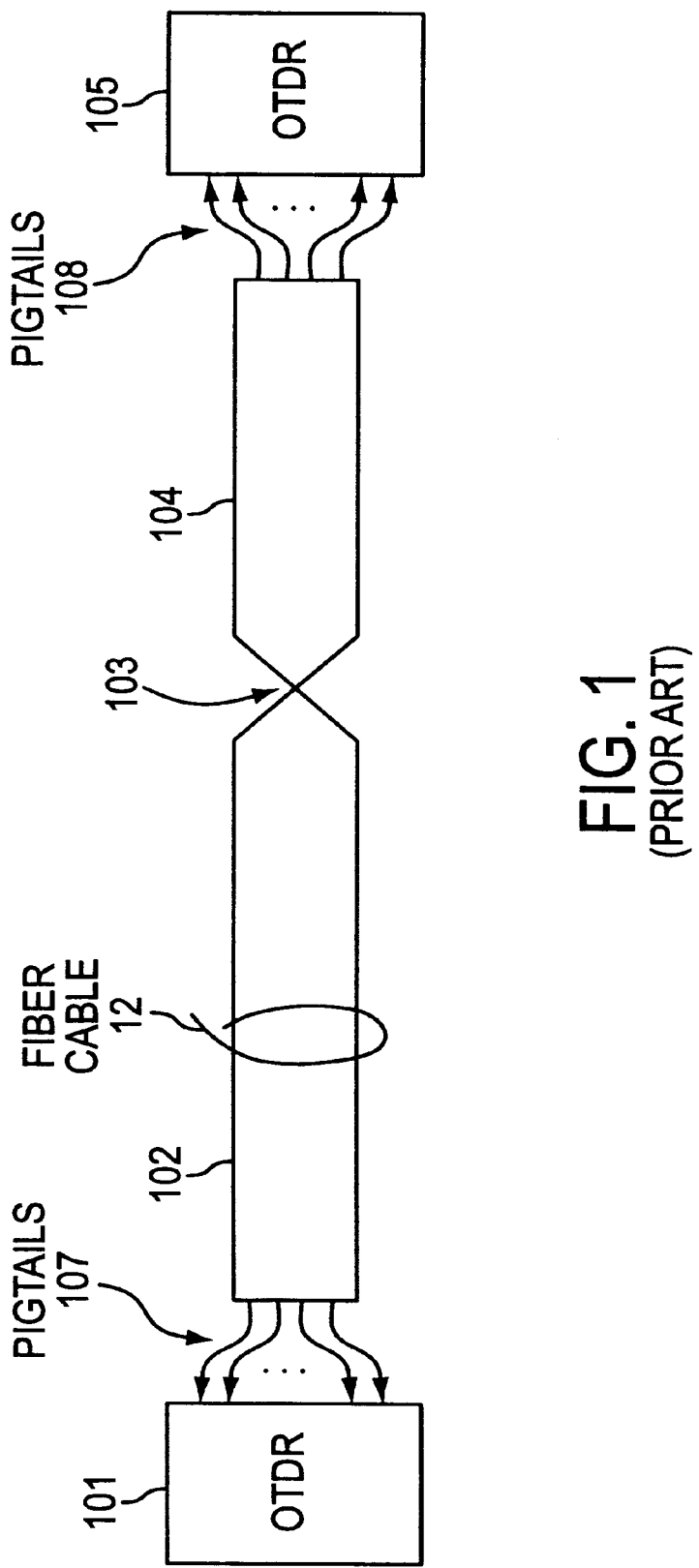
FIGS. 1–3 schematically illustrate prior art methods for testing and splicing fiber optic cable.
Figure 2:
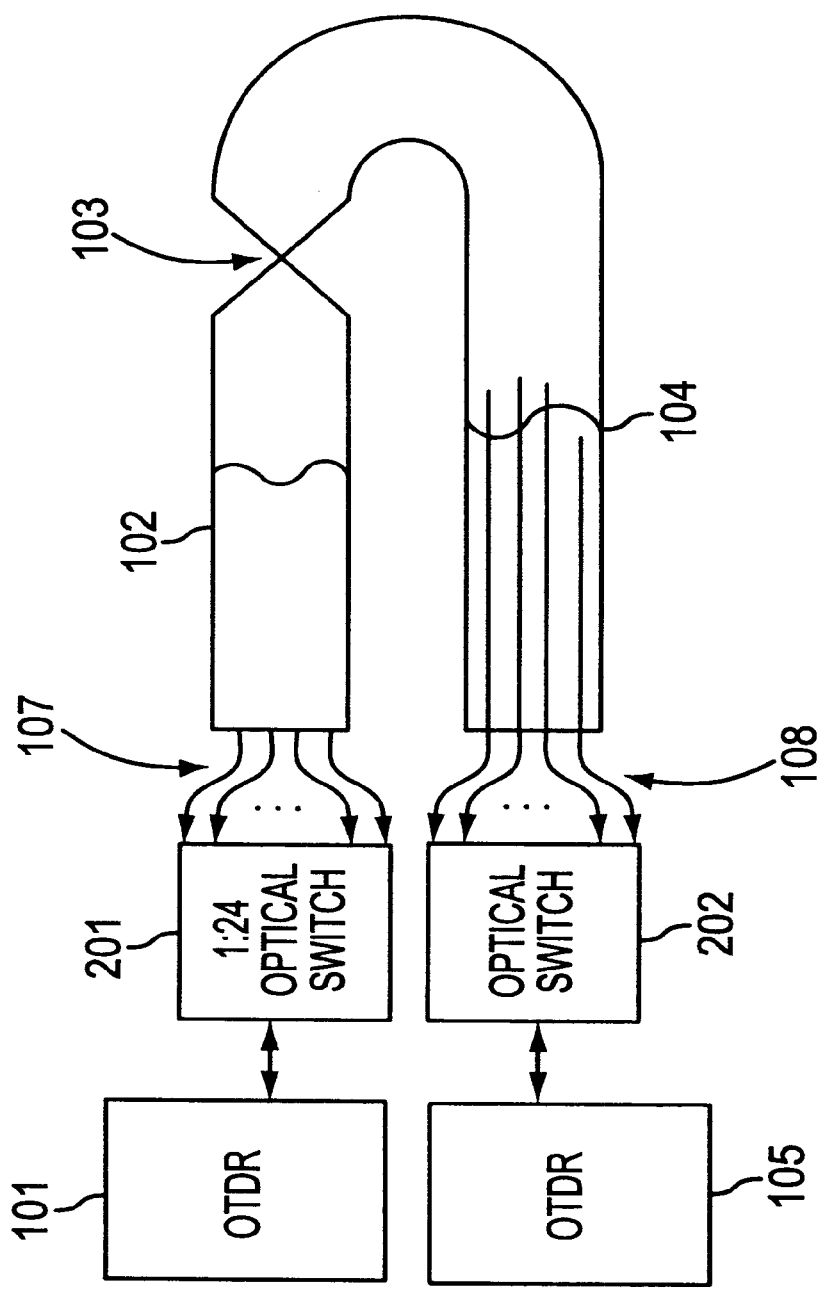
Figure 3:
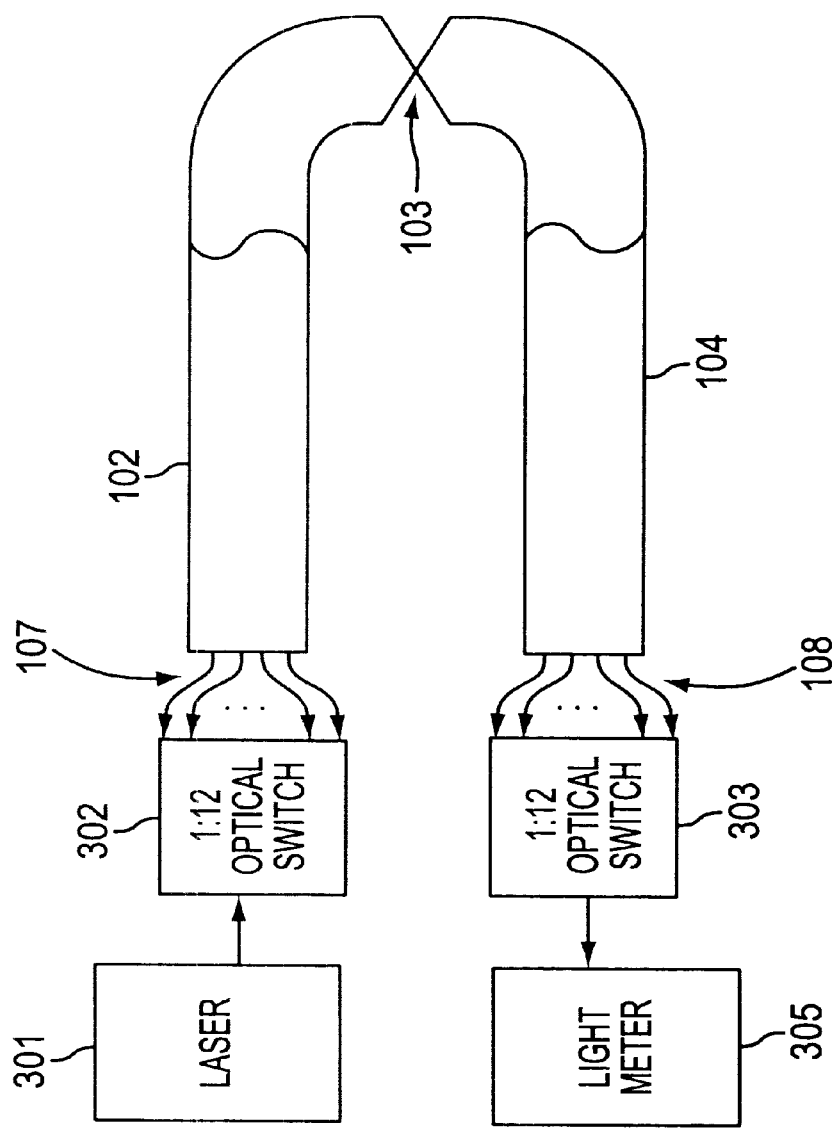
Figure 4:
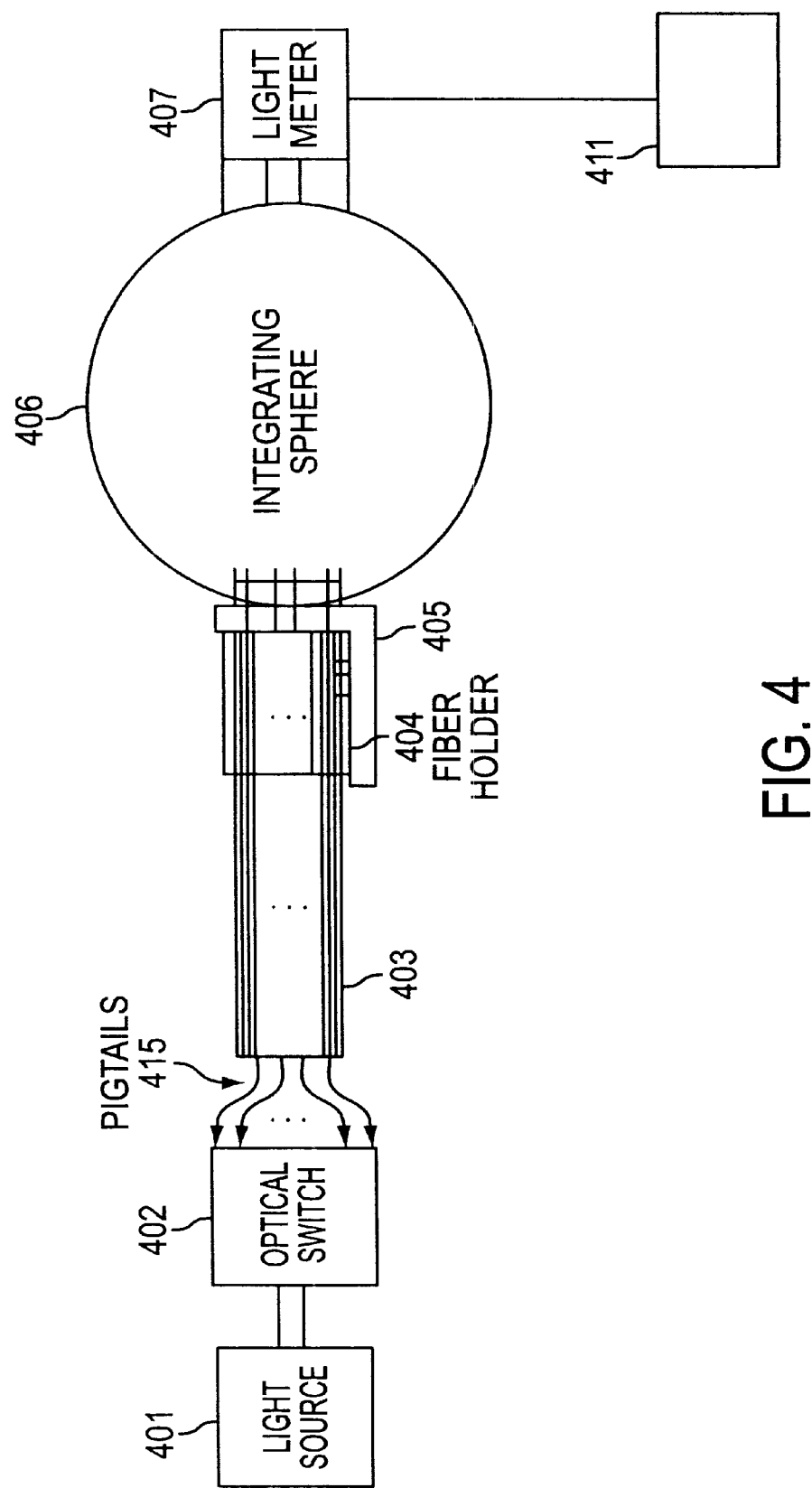
FIG. 4 schematically illustrates an exemplary embodiment of an optical fiber loss measurement system utilizing an integrating sphere.

FIG. 4 illustrates one exemplary embodiment of the present invention. As shown in FIG. 4, a first end of a fiber optic cable 403 may be connected to a light source 401 via optical switch 402. Light source 401 may be a laser of desirable wavelength that is capable of transmitting a light signal across long spans of fiber optic cable. In the alternative, the light source 401 may be a suitable LED (Light Emitting Diode) or any other suitable light source for transmitting light across fiber optic cable spans. Optical switch 402 may have one or more input ends and may have one or more output ends. The light source 401 may be coupled to, for example, the input end of the optical switch 402. The fiber optic cable 403 and/or other specimen or equipment under test may be connected to, for example, the output ends of the optical switch 402. At the first ends, fiber optic cable 403 may preferably be prepared (e.g., outer/inner protective jackets and/or buffer tubes are removed, individual fibers cleaned and cleaved, etc.) and the plurality of individual fibers connected to connectorized pigtails 415 or other mechanical connectors (not shown). Each of the connectors or pigtails may subsequently be coupled to the optical switch 402 at the output ends. In a preferred embodiment, fiber optical cable may be a multiple fiber ribbon cable having at least 12 individual fibers. Alternatively, the ribbon cable may have more than 12 individual fibers, for example, 16, 24, 36, 48, or 96 fibers or any other desirable number of individual optical fibers.

Referring again to FIG. 4, at the second ends, the fiber optic cable 403 may also be prepared (e.g., removal of the outer and inner jacket covering, cleaning and cleaving of the individual fiber, etc.) and subsequently installed in a fiber holder 404 (to be described below in more detail). The individual fibers may be set in the holder such that each fiber extends out of the holder 404 at a predetermined distance. In embodiments of the present invention, the fiber holder 404 with the plurality of optical fibers may be connected to an integrating sphere 406 (to be described below in more detail). The fiber holder 404 may be connected to the integrating sphere 406 either directly or using, for example, an adapter 405. Adapter 405 may be permanently affixed to the integrating sphere 406 or, in a preferred embodiment, may be detachable from the integrating sphere 406. The integrating sphere 406 may include two ports or openings, for example, one port for positioning of a sample to be tested and the second port for positioning of a measuring device, for example, a light meter 407. Once the exemplary configuration as shown in FIG. 4 is completed, a first reference measurement at integrating sphere 406 may be taken using light meter 407. A light signal at a predetermined power level may be transmitted from light source 401 through one or more of the plurality of individual fibers in fiber optic cable 403. The predetermined transmit power level may be, for example, +10 dB, +5 dB, 0 dB, −5 dB, −10 dB, −15 dB, etc. and or any other suitable power level. As is well known, the optical switch 402 permits the transmission of a light signal from light source 401 through each of the individual optical fibers. The optical switch 402 may be operated manually or may be operated automatically based on a preset time, for example. The light signal may be transmitted sequentially through each of the optical fibers separately and received at the integrating sphere 406. The light meter 407 can measure and display (not shown) the received signal levels representing the first set of reference measurements at the integrating sphere 406. As light is being sequentially received at integrating sphere 406, for each of the plurality of individual optical fibers, an operator may manually record the first set of reference measurements from the display. The first reference measurement may represent a signal level attenuated by losses that may be due to, for example, the cable 403, the optical switch 402, pigtails 415 and associated connectors, integrating sphere 406 and/or any other equipment, connectors or cables that may be installed between the light source 401 and light meter 407. In alternative embodiments of the present invention, reference measurements may be adjusted by a multiplication factor or a constant to compensate for desired losses. For example, adjustments may be made to compensate for losses of the integrating sphere 406, splices, connectors and or any other losses or requirements that may require compensation. Accordingly, the user may retrieve the received light levels for a particular optical fiber from the light meter 407, then multiply the retrieved level by the multiplication factor or constant to determine the first reference measurement.

In alternative embodiments of the present invention, the light meter 407 and/or attached device 411, for example, a PC or other intelligent device may automatically make and record the first reference measurement for each of the plurality of optical fibers. The light meter 407 and/or attached device 411 may automatically determine or request the user to enter the multiplication factor or constant and based on the entered data, the light meter 407 or attached device 411 may automatically determine the reference measurement levels of the optical fibers. Accordingly, by utilizing the integrating sphere 106, light meter 407 and/or attached device 411, the user may obtain a first reference measurement for each of the optical fibers within the cable 403 without having to attach pigtails to the second ends of the fiber optic cable 403 and without having to separately connect each fiber to the light meter 407.

In further alternative embodiments of the present invention, the light signal may be simultaneously transmitted through more than one optical fibers using the optical switch 402 and measured at the integrating sphere 406. The reference measurements and/or light losses for each of the optical fibers individually may be determined by known mathematically techniques. Under this embodiment, the attached intelligent device 411 may only require measurements from groups of optical fibers and based on the known groups and corresponding measurements and/or losses on individual fibers may be quickly and automatically determined by simple mathematical calculations.

Figure 5:
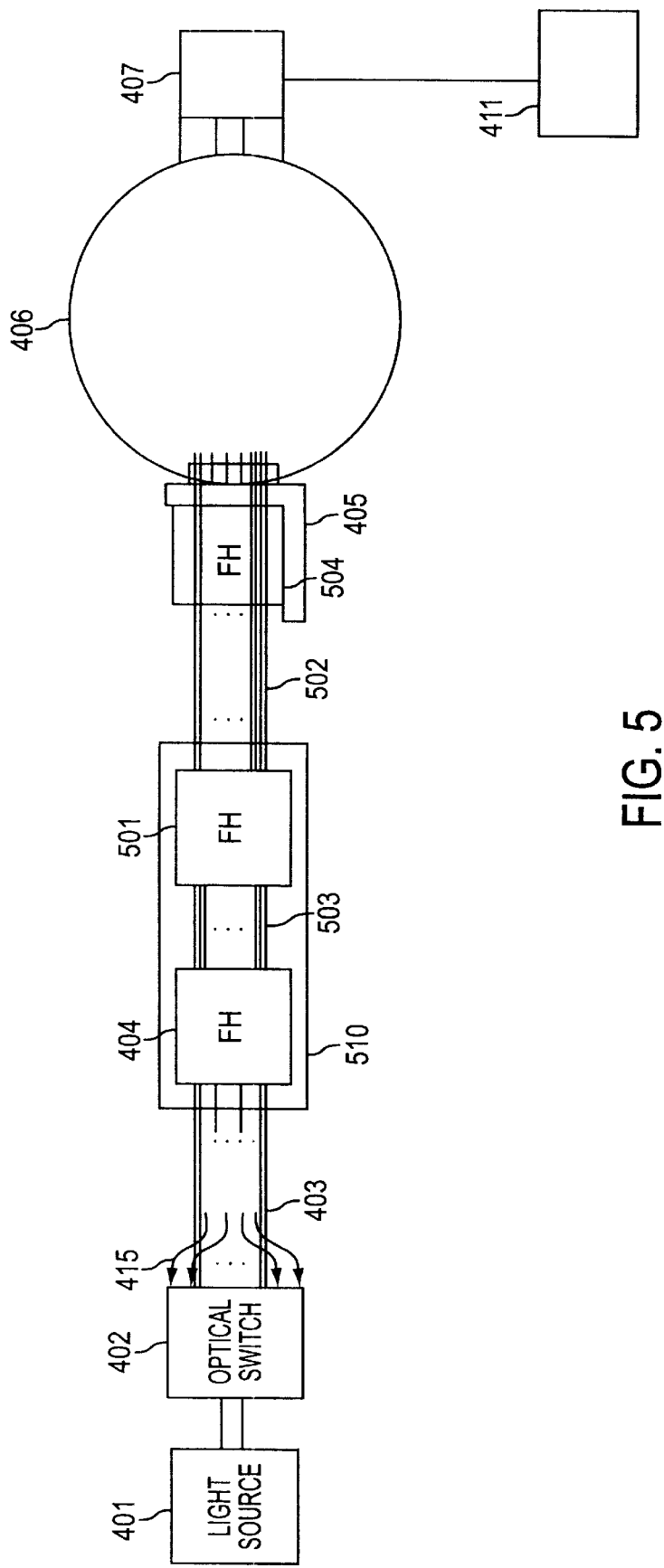
FIG. 5 schematically illustrates an exemplary embodiment of a mass fiber splicing and loss measurement technique utilizing a fiber holder.

FIG. 5 shows the embodiment of FIG. 4 with the addition of a fiber optic splicer and a second fiber optic cable. FIG. 5 illustrates an efficient method a determining "true loss" at a splice point as well as for determining the reliability of the splicer itself. Preferably, fiber optic cable 502 is similar to the fiber optic cable 403, in that cable 502 includes at least the same number of optical fibers as cable 403. In embodiments of the present invention, the length of the fiber cable 502 may be much shorter in comparison to the length of cable 403, so that the losses due to fiber cable 502 may be negligible. As illustrated in FIG. 5, first ends of fiber optic cable 502 may be coupled to a second fiber holder 501. Once the first reference measurements are taken as described above, fiber holder 404 may be removed from integrating sphere 406. Subsequently, fiber holders 404 and 501 may be placed in a mass fusion splicer 510 designed for splicing a plurality of fibers simultaneously. Mass fusion splicers are common and known. Individual fibers from optic cable 403 may be spliced to corresponding fibers from optic cable 502 using the mass fiber optical splicer 510. Under embodiments of the present invention, splicing efficiency may be significantly improved since the fiber holder 404 may be removed from the integrating sphere 406 and simply placed in mass fusion splicer 510 without any further preparation of the individual fibers (i.e., removal of the pigtails, cleaning, cleaving or stripping of the individual fibers, etc. as is required using conventional techniques).

Referring again to FIG. 5, after splicing of the fiber optic cables 403 and 502 has been completed, in embodiments of the present invention, a second reference measurement may be taken. In embodiments of the present invention, a third fiber holder 504 may be coupled to the second ends of the optical fiber 502. The third fiber holder 504 may be coupled to integrating sphere 406 using, for example, adapter 405. As described above, adapter 405 may be permanently affixed to the integrating sphere 406 or, in a preferred embodiment, may be detachable from the integrating sphere 406. Once the exemplary configuration as shown in FIG. 5 is configured, the second reference measurements at the integrating sphere 406 coupled to the second ends of the fiber optic cable 502 may be taken.

In embodiments of the present invention, a light signal of a predetermined power level may be transmitted from light source 401 through one of the plurality of optical fibers in the spliced fiber optic cables 403 and 502. The predetermined transmit power or light level may be, for example, +10 dB, +5 dB, 0 dB, −5 dB, −10 dB, −15 dB, etc. and or any other suitable power level. As light is transmitted sequentially through each of the optical fibers, light level readings representing the second reference measurements may be taken at the integrating sphere 406 for each of the optical fibers by the abovedescribed methods of the present invention. Accordingly, the "true loss" of splice point 503 may be determined by subtracting the second reference measurement from the first reference measurement for each of the plurality of individual optical fibers. The resulting difference represents the "true loss" of the optical splice excluding the additional losses that may be introduced by, for example, the optical switch 402, the splices and connectors of pigtails 415, and/or fiber optic cables 403, 502. Accordingly, the reliability of, for example, mass fusion splicer 510 may be more accurately determined without additional external losses as described above.

With reference to FIG. 5, examples of automation features in embodiments of the present invention will be described in more detail. It is to understood that these automation features are given by way of example only and one of ordinary skill in the art can readily modify the present invention to include additional automation features. For example, in an embodiment of the present invention, the second reference measurements may be multiplied by a multiplication factor or constant to compensate, for example, for the integrating sphere 406, mass splice losses, connector losses and or any other losses that may require compensation. Accordingly, the user or craftsperson may retrieve the received light levels received at the light meter 407, then multiply the retrieved level by the multiplication factor and finally, subtract the result from the calculated first reference levels to determine the "true loss" of the optical splice. In alternative embodiments of the present invention, the light meter and/or attached device 411, for example, a PC or other intelligent device may automatically record the second reference measurement at the integrating sphere 406. The light meter 407 and/or attached device 411 may automatically determine or request the user to enter the multiplication factor or constant as well as the transmitted power level. Based on the entered data, the light meter 407 or attached device may automatically determine the "true loss" of the optical splice. In alternative embodiments of the present invention, the user may also be requested to enter the loss specifications and/or a range of acceptable loss levels for the mass fusion splicer under test, and based on this information the light meter 407 and/or attached device 411 may notify the user whether or not the mass fusion splicer fall in the acceptable range. Accordingly, utilizing integrating sphere 406 and light meter 407 and attached device 411, the user may obtain the status of each optical splice and the reliability of the mass fusion splicer without having to separately connect each fiber to the light meter 407 and make separate readings and/or calculations.

Figure 6:
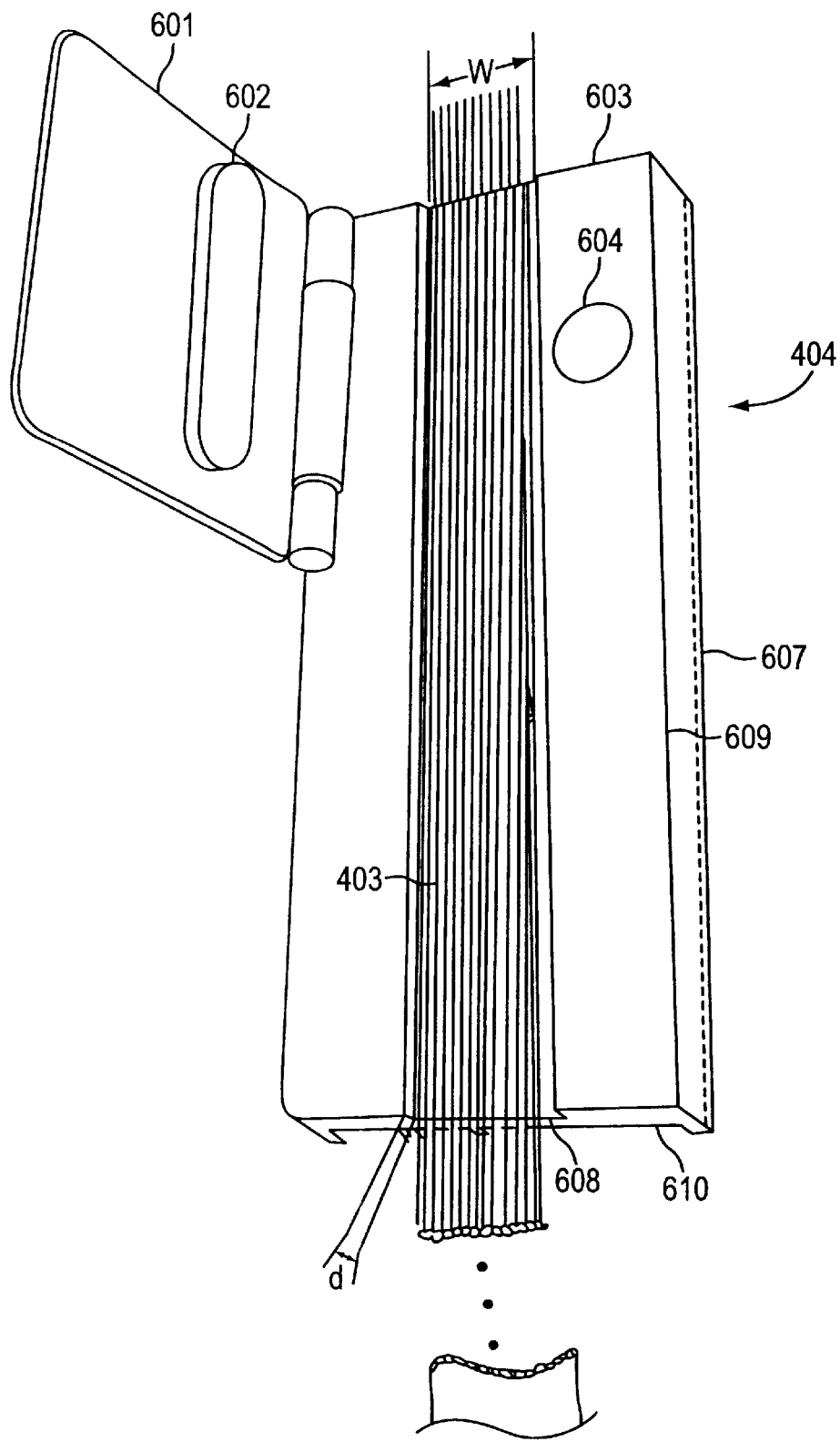
FIG. 6 illustrates an exemplary embodiment of a fiber optic holder.

FIG. 6 illustrates in further detail an exemplary embodiment of a fiber holder 404. The fiber holder 404 has a base section 609 that may include a longitudinal recessed channel 608 for holding, for example, a ribbon fiber optic cable 403. It is to be understood that ribbon fiber cable 502 and/or other suitable cable may be similarly installed in fiber holder 404. The channel 608 may extend along the entire length of the holder for securely holding the coated ribbon fiber therein. The channel 608 may be of a suitable width (w) and depth (d) to hold, for example, a coated multi-fiber ribbon cable. In a preferred embodiment, the channel 608 may hold a twelve (12) fiber ribbon cable. A cover 601 may be pivotally attached to base section 607 by a hinge and may include a downwardly depending block 602. A magnet 604 may be mounted in the surface of the base section 609 disposed on the side of the recessed channel 608. The magnet 604 may function to magnetically couple the cover 601 with the base section 609. To couple the ribbon fiber cable 403 to the fiber holder 404, the cover 601 is opened and the ribbon fiber cable 403 is inserted into the channel 608 with a predetermined length of the individual fibers (that have been cleaned, cleaved, measured, etc.) extending in front of the leading edge 603 of the base section 609. The optical fibers may be cleaned, cleaved and/or measured to the predetermined length by any suitable tool and/or device. The cover 601 may then be closed and the downwardly depending block 602 fills the recessed channel 608 and fictionally holds the coated ribbon fiber cable 403 in the channel 608. In a preferred embodiment, the magnet 604 provides an attraction force with the pivotable cover 601, which is metallic, to maintain a suitable force on the fiber cable 403. It is to understood that the fiber holder 404 and cover 601 may be made of any suitable material, for example, plastic, etc. and the cover may be coupled with the base section 609 by other locking arrangement. In lieu of a single recessed channel 608, fiber holder 404 may include a plurality of recessed channels for holding smaller groups or individual fibers.

The bottom end 607 of base section 609 may include a second recessed channel 610 for coupling the fiber holder 404 with, for example, adapter 405 (to be described below in more detail) and/or temporarily installed in a mass splicer. The recessed channel 610 may be of a suitable width and depth to permit the holder 404 to be coupled to the adapter 405. The recess 610 could be sloped complementary to a projection on the splicer and/or the adapter 405. It is recognized that the fiber holder 404 may include one or more projections and one or more complementary sloped grooves can be located on the splicer and/or the adapter 405. In a preferred embodiment, fiber holders 501 and 504 may share the same structure and/or size as fiber holder 404 illustrated in FIG. 5 and described above. In alternative embodiments, fiber holders 501 and 504 may have differing size and structure as may be desired. Fiber holders as shown in FIG. 6 are known in the art. These fiber holders are available in different widths for different splicing applications and with different groove or channel sizes for receiving different sized fibers. Moreover, fiber holders 404, 501 and 504 may include right hand and left hand orientations for simultaneous opening when the exposed and stripped free ends are spliced. Once the fiber cable 403 has been installed in the holder 404, for example, the holder 404 may be installed in a mass fiber optic splicer and/or an adapter 405.

Figure 7:
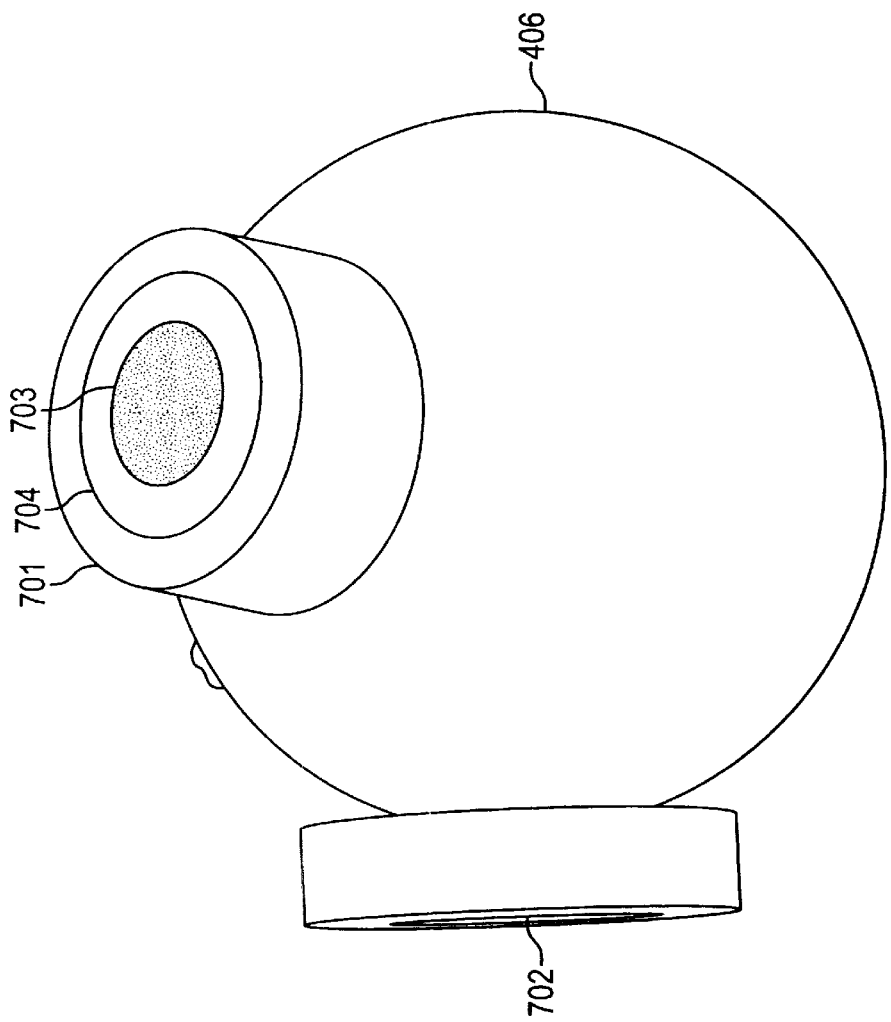
FIG. 7 illustrates an example of an integrating sphere for use in embodiments of the present invention.

FIG. 7 illustrates an exemplary embodiment of the integrating sphere 406. An integrating sphere is an instrument for measuring the total luminous flux of, for example, a lamp and/or other light source. The integrating sphere may include, for example, an input end 701 and an output end 702. The input end 701 of the integrating sphere 406 may include a cylindrical or other shaped opening 703 surrounded by metal collar 704. In embodiments of the present invention, and as described above, an adapter 405 may be removably coupled to, for example, the input end 701 of the integrating sphere 406. The adapter 405 may be used to couple the fiber holders with the integrating sphere 406. In alternative embodiments of the present invention, the fiber holder 404 may be shaped to directly connect to the input end 701 of the integrating sphere 406. In embodiments of the present invention, a light meter may be coupled to, for example, the output end 702 of the integrating sphere. Integrating spheres 406 of this type are known in the art and readily available. One such integrating sphere is sold by Hewlett Packard as Model No. HP 81002FF.

In exemplary embodiments of the present invention, the plurality of optical fiber ends is inserted into to the integrating sphere 406 at input 701. The light signal transmitted from the light meter may be introduced into the integrating sphere 406 from the plurality of optical fiber ends. The light introduced into the integrating sphere 406 reflects randomly off the inside walls until it achieves a uniform, spatially integrated distribution. The inner surface of the integrating sphere 406 may be made from one or more known reflective materials. The incoming light signal may be reflected inside the integrating sphere 406 and focus on a focal point within the integrating sphere. In embodiments of present invention, the focal point may focus on the output 702 of the integrating sphere 406 such that the light meter coupled to the integrating sphere 406 may be able to receive the focused signal. Accordingly, the light meter may measure and display the incoming light levels at the integrating sphere 406. In the alternative, the light meter may be calibrated to adjust for characteristics of the integrating sphere. Accordingly, in embodiments of the present invention, the light meter may determine the actual light levels received at the integrating sphere 406 based only on a portion of the light measured by the light meter. In alternative embodiments, a constant (i.e., a fixed number) may be required for a more accurate light level reading. For example, the constant may incorporate the characteristics of the integrating sphere 406 as well as account for fiber optic losses, and or splice loses.

Figure 8:
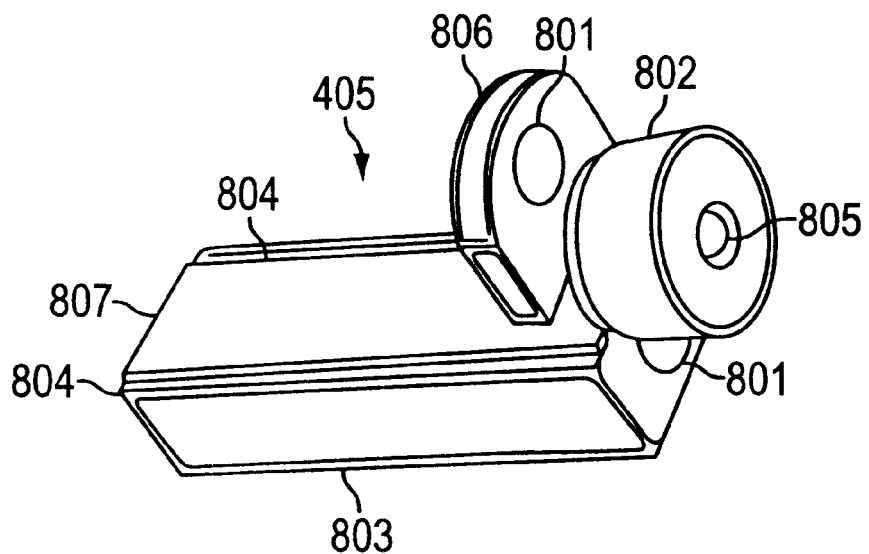
FIGS. 8 and 9 illustrate an exemplary embodiment of an adapter for a fiber holder.
Figure 9:
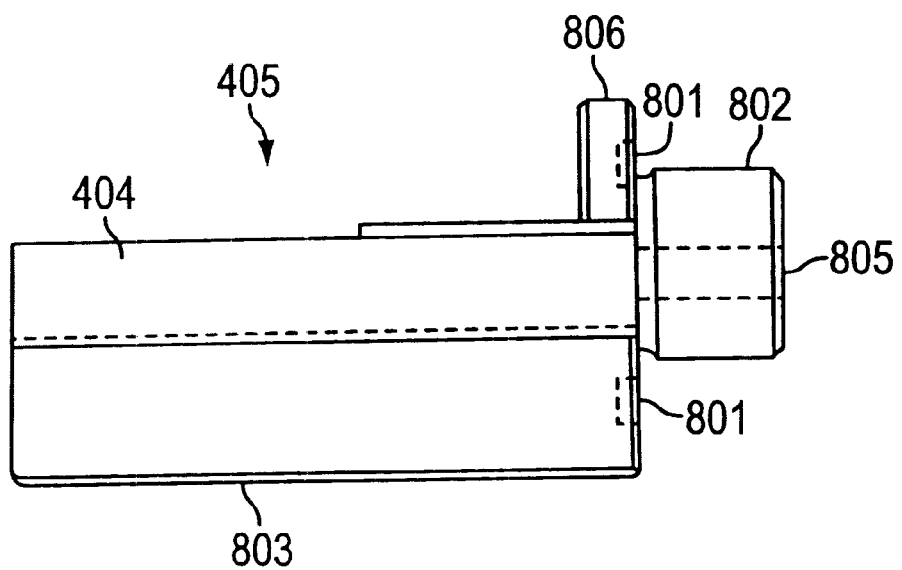

FIGS. 8 and 9 illustrate an exemplary embodiment of adapter 405. As shown, the adapter 405 may have a cylindrical protruding end 802 having an opening 805. The cylindrical end 802 is preferably of suitable size for insertion into input opening 703 of integrating sphere 406. The opening 805 may be of suitable shape and size, and run the entire depth of the cylindrical end 802 to permit the optical fibers to extend out from the leading edge 603 of holder 404 and out of the opening 805. Although opening 805 is illustrated in the form of a circle, it is to be understood that the opening 805 may be square, rectangular or any other suitable shape to permit the plurality of optical fibers to extend out from the cylindrical end 802. Embodiments of the adapter 405 may include any desirably shaped attachment member 806 for housing a magnet 801. The base section 803 of adapter 405 may further include magnet 801. The magnets 801 are spaced to couple the adapter 405 with the metallic collar 704 of the integrating sphere 406 at the input 701. As illustrated in FIGS. 8 and 9, the adapter base 803 may include a projecting ledge 807 or rails/notches 804 for slidably coupling fiber holder 404 using recess 610. It is recognized that the projecting ledge 807 and/or notches 804 may be of any desirable shape or size for coupling with the recess 610 of fiber holder 404. Once the fiber holder 404 containing the optical fiber ribbon 403 is coupled to adapter 405, holder 404 and adapter 405 assembly may be coupled to the integrating sphere 406 by inserting the cylindrical end 802 into the opening 703 of input 701.

In operation, embodiments of the present invention disclose a time, labor and cost efficient system and method for testing the reliability of optical splices. The reliability of the optical splices determined by the disclosed method and system corresponds to the reliability of the optical splicers themselves. As described above and shown in FIGS. 4–8, a first fiber optic cable including a plurality of optical fibers is coupled to a light source and optical switch at one end. Light may be transmitted through the plurality of optical fibers individually (i.e., one at a time) or simultaneously through more than one of the optical fibers. At the other end of the first fiber optic cable, the plurality of optical fibers is simultaneously coupled to a fiber holder. The fiber holder is then coupled to an integrating sphere and first set of reference measurements can be quickly taken at the integrating sphere using a light meter without replacing pigtail connectors and using another optical switch. The fiber holder including the plurality of fibers can be coupled to the integrating sphere either directly or using the adapter as described and illustrated herein. Under this configuration, light simultaneously transmitted through more than one optical fiber may be measured at the integrating sphere using the light meter and the first reference measurements for each of the individual fibers may be mathematically determined to further improve time efficiency. The first reference measurement represent the loss of the optical switch, any interposed pigtail connectors or splices and the loss through the optical fibers.

Once the first reference measurements are taken, the fiber holder including the plurality of optical fibers is removed from the integrating sphere and coupled to a mass fiber fusion splicer. A second cable including a plurality of optical fibers is coupled to another fiber holder and coupled to the mass fusion splicer. The plurality of optical fibers from the first cable is spliced with the plurality of optical fibers from the second cable. The plurality of optical fibers at the other end of the second cable is coupled to a third fiber holder. The third fiber holder is coupled to the integrating sphere either directly or using the adapter. A second set of reference measurement readings is taken at the integrating sphere. Similar to the above configuration, light can be simultaneously transmitted through more than one of the spliced optical fibers. The transmitted light through more than one fiber can be measured at the integrating sphere using the light meter and the second reference measurements for each of the individual fibers may be mathematically determined so that even less time is required. The second reference measurement represent the loss of the optical switch, any interposed pigtail connectors or splices, the loss through the optical fibers of the first cable and the loss at the splice point. The loss of through the fibers of the second cable may be negligible. By subtracting the second reference measurements from the first, an accurate loss measurement at the splice point can be determined.

Under embodiments of the invention, the reliability of the splices can be quickly determined. The reliability of the optical splices determined by the disclosed method and system corresponds to the reliability of the mass optical splicers themselves. In lieu of connecting the plurality of spliced optical fibers to the light meter using additional pigtails and a second optical switch, under embodiments of the present invention, the plurality of optical fibers are simultaneously connected to the integrating sphere coupled to the light meter. Accordingly, the losses introduced by the additional pigtails and the floating losses of the second optical switch are eliminated. The configuration under the present invention is additionally advantageous since losses can be determined even more efficiently by mathematical calculations and/or coupling the light meter to an intelligent device.

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

I claim:

1. A method for measuring a loss through optical fibers, the method comprising the steps of:

providing a first fiber optic cable having a plurality of optical fibers with first and second ends;

coupling the plurality of optical fibers at the first ends to an output end of an optical switch;

coupling the plurality of optical fibers at the second ends to a first fiber holder;

attaching the first fiber holder to an adapter;

coupling the adapter to an input end of an integrating sphere to optically couple each of the plurality of optical fibers to the integrating sphere;

coupling an input end of the optical switch to a light source, the light source capable of delivering light of a known quantity to the optical switch;

transmitting light through each of the plurality of optical fibers from the first ends to the integrating sphere including activating the optical switch such that the light is transmitted through each of the plurality of optical fibers; and measuring a quantity of light received at the integrating sphere passing through at least one of the plurality of optical fibers.

2. The method as recited in claim 1, wherein the measuring step comprises:

coupling an output end of the integrating sphere to a light meter; and measuring the quantity of light received for each of the plurality of optical fibers at the integrating sphere using the light meter.

3. The method as recited in claim 2, further comprising the steps of:

automatic switching by the optical switch such that light is automatically transmitted through the plurality of optical fibers one at a time.

4. The method as recited in claim 3, further comprising the steps of:

storing the measured light for each of the optical fibers received at the integrating sphere.

5. The method as recited in claim 2, further comprising the steps of:

receiving inputs representing the measured quantity of light received at the integrating sphere for each of the plurality of optical fibers, said inputs representing a first reference measurement for each of the plurality of optical fibers.

6. The method as recited in claim 5, further comprising the steps of:

removing the adapter and attached first fiber holder from the integrating sphere;

coupling the first fiber holder in a mass fiber fusion splicer;

providing a second fiber optic cable having a plurality of optical fibers with first and second ends;

coupling the plurality of first ends of the fibers of the second cable to a second fiber holder;

attaching the second fiber holder to the adapter;

coupling the second fiber holder in a mass fiber fusion splicer; and splicing the plurality of second ends of the fibers of the first cable with the first ends of the fibers of the second cable at a splice point.

7. The method as recited in claim 6, further comprising the steps of:

coupling the second ends of the fibers of the second cable to the integrating sphere;

repeating the step of transmitting the light through each of the plurality of optical fibers from the first ends of the fibers of the first cable;

measuring the quantity of light received for each of the plurality of optical fibers at the integrating sphere, the measurement received at the integrating sphere coupled to the second ends of the fibers of the second cable representing a second reference measurement for each of the plurality of optical fibers; and determining for each of the plurality of fibers a loss at the splice point by subtracting the second reference measurement from the first reference measurement for each of the plurality of optical fibers.

8. The method as recited in claim 7, wherein the light is transmitted through each of the plurality of optical fibers one at a time.

9. The method as recited in claim 1, further comprising the step of:

repeating the transmitting and measuring step; and determining the quantity of light through each of the individual optical fiber.

10. A system for testing fiber optic cable segment having a plurality of optical fibers having first and second ends, the system comprising:

an integrating sphere coupled to a first fiber cable segment at the second ends of the fibers;

a light source being optically coupled to the first ends of the fibers of the first cable segment for transmitting a light signal through each of the fibers;

a first fiber holder for holding the plurality of second ends of the first fiber cable segment;

a second fiber holder for holding the plurality of optical fibers of a second fiber cable segment at their first ends, wherein the second fiber holder is removably coupled to a mass fiber fusion splicer for splicing the second ends of the plurality of optical fibers of the first cable segment with the first ends of the plurality of optical fibers of the second cable segment;

an adapter for coupling the second ends of the second fiber cable segment with the integrating sphere;

a third fiber holder for holding the plurality of optical fibers of the second fiber cable segment at their second ends;

wherein the third fiber holder is removably coupled to the adapter such that second ends of the second fiber cable segment are optically coupled to the integrating sphere; and a light meter for measuring a first quantity of light signal received at the integrating sphere transmitted through at least one of the plurality of optical fibers.

11. The system as recited in claim 10, wherein the optical fibers of the first fiber optic cable segment are spliced to respective optical fibers in the second fiber optic cable segment, the light meter is further adapted for use to measure a second quantity of light signal received at the integrating sphere, the second quantity of light signal being lesser than the first quantity of light signal and being transmitted through at least one of the plurality of spliced optical fibers.

12. The system as recited in claim 11, further comprising an intelligent device being coupled to the light meter, the intelligent device comprising:

a receiver for receiving the first quantity of light signal and the second quantity of light signal; and a processor for determining a difference between the first light signal and the second light signal, the difference indicating the reliability of the splice.

13. The system as recited in claim 11, wherein the intelligent device further comprising:

a display for displaying the difference.

14. The system as recited in claim 10, further comprising:

an optical switch having an input side and an output side for optically coupling the light source with the first ends of the fibers of the first cable segment, wherein the light source is coupled to the optical switch at the input side and the first ends of the fibers of the first cable segment are coupled to the optical switch at the output side, wherein the optical switch permits the transmission of light signal from the light source through each of the plurality of optical fibers.

15. A method for determining a loss through at least one optical fiber of a first fiber optic cable, the first fiber optic cable having a plurality of optical fibers with first and second ends, the method comprising the steps of:

coupling a light source to the first ends of the plurality of optical fibers;

attaching the second ends of the plurality of optical fibers to a first fiber holder;

optically coupling the second ends of the plurality of optical fibers to an integrating sphere by attaching the first fiber holder to an adapter and coupling the adapter to the integrating sphere;

transmitting a first light signal of a known quantity along the plurality of optical fibers using the light source;

measuring a transmitted first light signal at the integrating sphere;

removing the first fiber holder from the adapter;

installing the first fiber holder in a mass fusion splicer;

providing a second fiber optic cable having a plurality of optical fibers with first and second ends;

placing the first ends of the plurality of optical fibers of the second cable in a second fiber holder;

installing the second holder in the mass fusion splicer and splicing at a splice point the second ends of the plurality of optical fibers of the first cable with the first ends of the plurality of optical fibers of the second cable;

placing the second ends of the plurality of optical fibers of the second cable in a third fiber holder;

optically coupling the third fiber holder to the integrating sphere;

transmitting a second light signal of the known quantity along the plurality of spliced optical fibers using the light source; and measuring the transmitted second light signal received at the integrating sphere.

16. The method as recited in claim 15, wherein the step of optically coupling the third fiber holder to the integrating sphere comprises:

attaching the third fiber holder to the adapter; and coupling the adapter to the integrating sphere.

17. The method as recited in claim 15, further comprising the steps of:

determining the difference between the measured first light signal and the measured second light signal at the integrating sphere, wherein the difference represents a loss at the splice point.

18. A system for determining a loss through at least one optical fiber of a first fiber optic cable, the first fiber optic cable having a plurality of optical fibers with first and second ends, the system comprising:

a light source coupled to the first ends of the plurality of optical fibers and adapted to transmit a first light signal and a second light signal;

a first fiber holder for coupling to the second ends of the plurality of optical fibers;

an integrating sphere;

a mass fusion splicer, wherein the first fiber holder is installed in the mass fusion splicer;

a second fiber optic cable having a plurality of fibers with first and second ends;

a second fiber holder for coupling to the first ends of the plurality of optical fibers of the second cable, wherein the second fiber holder is installed in the mass fusion splicer and wherein the splicer is used to optically splice the second ends of the plurality of optical fibers of the first cable with the first ends of the plurality of optical fibers of the second cable at a splice point;

a third fiber holder for holding the second ends of the plurality of optical fibers of the second cable;

an adapter, wherein the third fiber holder is coupled to the adapter and the adapter is coupled to the integrating sphere such that the second ends of the second fiber optical cable are optically coupled to the integrating sphere; and a light meter for measuring a first transmitted light signal and second transmitted light signal at the first integrating sphere.

19. The system as recited in claim 18, further comprising:

a receiver for receiving a first input representing the measured first light signal and a second input representing the measured second light signal at the integrating sphere; and a processor for calculating a difference between the first input and the second input, wherein the difference represents a loss at the splice point.

20. A system for testing fiber optic cable segment having a plurality of optical fibers having first and second ends, the system comprising:

an integrating sphere coupled to a first fiber cable segment at the second ends of the fibers;

a light source being optically coupled to the first ends of the fibers of the first cable segment for transmitting a light signal through each of the fibers;

a first fiber holder for holding the plurality of second ends of the first fiber cable segment;

a second fiber holder for holding the plurality of optical fibers of a second fiber cable segment at their first ends, wherein the second fiber holder is coupled to a mass fiber fusion splicer for splicing the second ends of the plurality of optical fibers of the first cable segment with the first ends of the plurality of optical fibers of the second cable segment;

a third fiber holder for holding the plurality of optical fibers of the second fiber cable segment at their second ends, wherein the third fiber holder is coupled to the integrating sphere such that the second ends of the plurality of optical fibers of the second fiber cable segment are optically coupled to the integrating sphere;

a light meter for measuring a first quantity of light signal received at the integrating sphere transmitted through at least one of the plurality of optical fibers.

21. The system as recited in claim 20, wherein the optical fibers of the first fiber optic cable segment are spliced to respective optical fibers in the second fiber optic cable segment.

22. The system as recited in claim 21, further comprising an intelligent device being coupled to the light meter, the intelligent device including a receiver for receiving multiple light signals and a processor for determining a difference between the multiple sensed light signals, the difference indicating the reliability of the splice.

23. The system as recited in claim 21, wherein the intelligent device further including a display for displaying the difference.

24. The system as recited in claim 20, further comprising:

an optical switch having an input side and an output side for optically coupling the light source with the first ends of the fibers of the first cable segment, wherein the light source is coupled to the optical switch at the input side and the first ends of the fibers of the first cable segment are coupled to the optical switch at the output side, wherein the optical switch permits the transmission of light signal from the light source through each of the plurality of optical fibers.

25. A method for determining a loss through at least one spliced optical fiber of first and second fiber optic cables, the first and second fiber optic cables each having a plurality of optical fibers with first and second ends, the method comprising the steps of:

coupling a light source to the first ends of the plurality of optical fibers of the first cable;

attaching the second ends of the plurality of optical fibers of the first cable to a first fiber holder;

optically coupling the second ends of the plurality of optical fibers of the first cable to an integrating sphere;

transmitting a first light signal of a known quantity along the plurality of optical fibers using the light source; and measuring the transmitted first light signal at the integrating sphere;

installing the first fiber holder in a mass fusion splicer;

placing the first ends of the plurality of optical fibers of the second cable in a second fiber holder;

installing the second holder in the mass fusion splicer and splicing at a splice point the second ends of the plurality of optical fibers of the first cable with the first ends of the plurality of optical fibers of the second cable;

placing the second ends of the plurality of optical fibers of the second cable in a third fiber holder;

optically coupling the third fiber holder to the integrating sphere;

transmitting a second light signal of the known quantity along the plurality of spliced optical fibers using the light source; and measuring the transmitted second light signal received at the integrating sphere.

26. The method as recited in claim 25, wherein the step of optically coupling the third fiber holder to the integrating sphere including attaching the third fiber holder to an adapter; and coupling the adapter to the integrating sphere.

27. The method as recited in claim 25, further comprising the steps of: determining the difference between the measured first light signal and the measured second light signal at the integrating sphere, wherein the difference represents a loss at the splice point.

28. A system for determining a loss through at least one spliced optical fiber of first and second fiber optic cables, the first and second fiber optic cables each having a plurality of optical fibers with first and second ends, the system comprising:

- a light source coupled to the first ends of the plurality of optical fibers of the first cable;
- a first fiber holder for coupling to the second ends of the plurality of optical fibers of the first cable;
- an integrating sphere;
- a mass fusion splicer, wherein the first fiber holder is installed in the mass fusion splicer;
- a second fiber holder for coupling to the first ends of the plurality of optical fibers of the second cable, wherein the second fiber holder is installed in the mass fusion splicer and wherein the splicer is used to optically splice the second ends of the plurality of optical fibers of the first cable with the first ends of the plurality of optical fibers of the second cable at a splice point;
- a third fiber holder for holding the second ends of the plurality of optical fibers of the second cable, wherein the second ends of the plurality of optical fibers of the second cable are optically coupled to the integrating sphere;

wherein the light source is further adapted for use to transmit a first light signal and a second light signal along the plurality of spliced optical fibers; and a light meter is adapted for use to measure the transmitted first light signal and second light signal at the integrating sphere.

29. The system as recited in claim 28, further comprising:

- a receiver for receiving a first input representing the measured first light signal and a second input representing the measured second light signal at the integrating sphere; and
- a processor for calculating a difference between the first input and the second input, wherein the difference represents a loss at the splice point.

* * * * *